United States Patent
Linford et al.

(10) Patent No.: US 9,150,419 B2
(45) Date of Patent: Oct. 6, 2015

(54) POLYCRYSTALLINE ARTICLES FOR REAGENT DELIVERY

(75) Inventors: Matthew R. Linford, Orem, UT (US); Michael A. Vail, Genola, UT (US)

(73) Assignees: US SYNTHETIC CORPORATION, Orem, UT (US); BRIGHAM YOUNG UNIVERSITY, Provo, UT (US)

( * ) Notice: Subject to any disclaimer, the term of this patent is extended or adjusted under 35 U.S.C. 154(b) by 898 days.

(21) Appl. No.: 12/463,413

(22) Filed: May 10, 2009

(65) Prior Publication Data

US 2010/0096587 A1    Apr. 22, 2010

Related U.S. Application Data

(60) Provisional application No. 61/052,186, filed on May 10, 2008.

(51) Int. Cl.

| | |
|---|---|
| *C09K 3/00* | (2006.01) |
| *C01B 31/06* | (2006.01) |
| *B01L 3/00* | (2006.01) |
| *A61J 3/07* | (2006.01) |
| *B29C 39/10* | (2006.01) |
| *B01J 3/06* | (2006.01) |
| *B01J 3/08* | (2006.01) |
| *B32B 3/26* | (2006.01) |
| *G01N 35/10* | (2006.01) |

(52) U.S. Cl.
CPC . *C01B 31/06* (2013.01); *B01L 3/52* (2013.01); *B01L 2200/12* (2013.01); *B01L 2300/12* (2013.01); *G01N 35/1002* (2013.01)

(58) Field of Classification Search
USPC .......... 252/182.32; 264/4, 128, 628; 423/446; 427/212; 428/304.4, 403; 436/8
See application file for complete search history.

(56) References Cited

U.S. PATENT DOCUMENTS

| | | | |
|---|---|---|---|
| 2004/0118762 A1 | 6/2004 | Xu et al. | |
| 2005/0158549 A1 * | 7/2005 | Khabashesku et al. | 428/403 |
| 2008/0028839 A1 * | 2/2008 | Vail | 73/64.56 |
| 2008/0070308 A1 * | 3/2008 | Ruhland et al. | 436/8 |

FOREIGN PATENT DOCUMENTS

| | | | | |
|---|---|---|---|---|
| EP | 0158825 A1 * | 10/1985 | | B24O 3/10 |
| KR | WO2005/068114 A1 * | 7/2005 | | B22F 7/02 |
| WO | WO 00/38655 * | 7/2000 | | |

OTHER PUBLICATIONS

Lang Li a, J.L. Davidson b, Charles M. Lukehart, Surface functionalization of nanodiamond particles via atom transfer radical polymerization, Carbon 44 (2006) 2308-2315, www.elsevier.com/locate/carbon,2006 Elsevier Ltd. All rights reserved.*
E. A. Ekimov, E. L. Gromnitskaya, S. Gierlotka, W. Lojkowski, B. Palosz, A. Swiderska-Sroda, J. A. Kozubowski, A. M. Naletov, Mechanical behavior and microstructure of nanodiamond-based composite materials,Journal of Materials Science Letters 21, 2002, 1699-1702, 2002 Kluwer Academic Publishers.*
Yushin, G.N. et al., Effect of sintering on structure of nanodiamond, Science Direct, Diamond & Related Materials 14 (2005) 1721-1729, Available online Aug. 10, 2005.
U.S. Appl. No. 61/052,185, filed May 10, 2008, Linford.
U.S. Appl. No. 61/052,186, filed May 10, 2008, Linford et al.

* cited by examiner

*Primary Examiner* — Bijan Ahvazi
(74) *Attorney, Agent, or Firm* — Dorsey & Whitney LLP

(57) ABSTRACT

A reagent delivering article comprising porous sintered polycrystalline diamond where the delivering article is capable of retaining at least one chemical reagent and releasing the chemical reagent in a fluid or has reactive sites on diamond surfaces of the article.

19 Claims, 1 Drawing Sheet

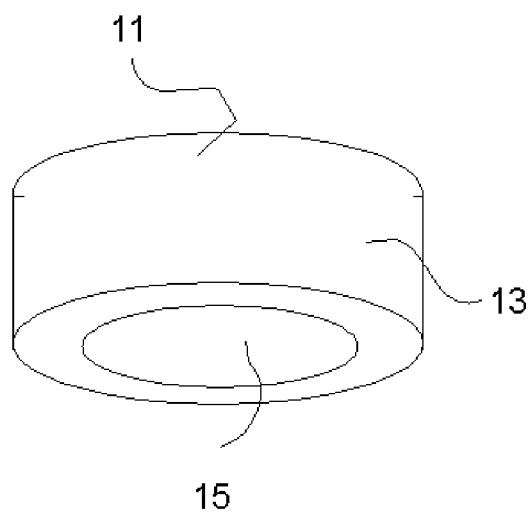

POLYCRYSTALLINE ARTICLES FOR REAGENT DELIVERY

CROSS REFERENCE TO RELATED APPLICATIONS

Priority is claimed from U.S. Provisional Patent Application 61/052,186, filed 10 May 2008, which is hereby incorporated by reference

BACKGROUND

U.S. patent application Ser. No. 11/597,786, Publication No. US2008070308, Serial, filed as PCT Application No. PCT/DK05/00428 on Jun. 27, 2005, which is hereby incorporated by reference, discloses a porous article for delivering chemical substance that is capable of retaining at least a chemical reagent and releasing the chemical reagent in a solvent.

SUMMARY

An aspect relates to a reagent delivering article comprising sintered diamond. Another aspect relates to reagent delivering articles capable of retaining liquid or solid reagents, a method of preparing said articles and the use of said articles for loading liquid reagents. Another aspect relates to reagent delivering articles retaining at least one chemical reagent, a method of preparing same and the use of said retained articles in solution phase chemistry, where said retained reagent is released from said articles into the solution.

An aspect provides a reagent delivering article consisting essentially of a polycrystalline diamond and an optional solid active substance, which reagent delivering article is capable of retaining at least one liquid reagent.

In another aspect the reagent delivering article can comprise polycrystalline diamond with an active surface, or with an inert or non-active surface. The polycrystalline diamond article is capable of retaining at least one liquid or solid reagent and is particularly useful in solution phase chemistry. Upon addition of the article to a solution, the reagent may be released from article. Thus, a predetermined fixed amount of reagent may be released to a reaction mixture.

Large numbers of the article can conveniently be prefabricated. The article can readily be distributed as such or be loaded automatically with predetermined amounts of different reagents commonly used in the field of chemistry. This may provide for a simple distribution of reagents, reduce exposure to hazardous substances, improve dosing precision and accuracy, and the articles are furthermore easy to implement in reactions, may make it possible to speed up the execution of syntheses, in particular synthesis of compound libraries and series, and reduce the complexity of synthesis operations (manual and automated).

Because the liquid or solid reagent is in the article, problems with handling statically charged reagents may be minimized, and the stability of functional groups may be increased.

In another aspect is a method for preparing said reagent delivering article; the method comprises forming polycrystalline diamond into a shape, and optionally treating the surface of the polycrystalline shape to impart activity to the surface. An alternate aspect involves compression forming a shape of polycrystalline diamonds bound by a polymer, with the optional addition of active solids, (such as catalysts), and liquid or solid reagents into the mixture from which the form is made.

In particular, an aspect relates to the use of a diamond reagent delivering article that can retain at least one liquid reagent and that, due to its diamond composition is inert with respect to the reagents and a reaction environment.

Another aspect is a reagent delivering article consisting essentially of a porous diamond article.

In particular, an aspect relates to reagent delivering articles for use in solution phase chemistry, whereby the retained liquid reagent(s) is released from the said article, particularly for use in parallel solution phase chemistry.

BRIEF DESCRIPTION OF DRAWINGS

FIG. 1 is a perspective view of one embodiment a polycrystalline article of the invention.

DETAILED DESCRIPTION

Reagent Delivering Articles

Reagents contained in a solid porous diamond articles may readily be released into a solvent, and therefore reagents can be delivered to a reaction medium from an inert polycrystalline diamond article. The reagent delivering polycrystalline diamond article has a predetermined shape and size and forms thereby a novel reagent delivering system for chemical reagents.

The reagent delivering article is capable of retaining liquid or solid reagents and subsequently releasing the reagent(s) in a fluid and thus can be seen as a porous reagent delivering article, device or system. The article and different embodiments thereof will now be described in detail below, including methods of preparing the article and use thereof.

The term "chemical reagent" should in this application be understood in the usual way (i.e. a compound or mixture of compounds that may take part in and be consumed in a chemical reaction).

The term "liquid reagent," as used herein, means any organic, inorganic, hydrophobic or hydrophilic liquid and any solid or liquid substance dissolved or dispersed in an organic, inorganic, hydrophobic or hydrophilic liquid. The liquid reagent may be a neat compound or a mixture of two or more compounds. It should be understood that the term liquid reagent includes not only compounds that are liquid at ambient temperature, but includes also reagents that are liquid only at higher or lower temperature.

The term "retaining," as used herein, means capable of holding within a defined amount of a reagent depending on the properties of the polycrystalline diamond article.

The term "solid active substance" means a substance having a function in a particular intended chemical reaction. Thus solid chemical active substances may for example be selected from the group containing solid reagents, metals, catalysts or scavengers.

Being comprised of polycrystalline diamond, the reagent delivering article remains essentially in the original form and does not substantially disintegrate when placed in reaction medium. Furthermore, such a reagent delivering article may be reused.

The term "reaction medium" is, in the present specification, intended to be understood in the usual meaning as a fluid (i.e. liquid, gas, supercritical fluid), and may include reagents, solvents, pH adjusting components, scavengers etc.

Because porous polycrystalline diamond is so tough, reagent could be dispensed into a gas phase by heating it to a temperature that would not affect the diamond matrix, but volatilize the compound trapped in the matrix. There are a variety of organic compounds that could be heated and evaporated this way. Examples might include processes for depolymerizing a polymer.

When it is no longer desired to have the article in a solution, a property of the reagent delivering article is that it may remain essentially in the original form. This makes the article easy to remove and/or discard, either because it does not block a filter process, or because the article can simply be removed, in virtue of it being intact, without any filtering.

The reagent delivering article optionally has a predetermined shape. The shape may be in any form, for example but not limited to, a sphere, ellipsoid, tablet, bar cylinder, or the like. The shape of the article is not limiting of the function of the article to retain liquid reagents but is a means of varying the article in order to adapt to storage and packaging of the article, convenience in production and use in different reaction vessels having different shapes and dimensions. Furthermore the reagent delivering article may be adapted to a specific tool such as a dispenser for dispensing the reagent delivering article.

The reagent delivering article may be provided with a string or other device in order to ease addition and removal of the device, similar to the principle known from teabags. Other known measures for easy removal of the device from a solution (e.g. tweezers, inclusion of a magnetic material for magnetic removal) are also contemplated.

Packaging of the loaded reagent delivering articles in e.g. blister packs is further contemplated. In addition to being convenient, packaging the reagent delivering articles may protect the reagent delivering articles against mechanical impact, moisture, oxygen etc. and will further protect users thereof against the reagent loaded in the articles (e.g. against fumes of volatile reagents). Such blister packs may even be designed to allow simultaneous dispensing of all articles in a blister pack into an array of reaction tubes or wells, such as a microtiterplate.

In still another embodiment, any of the articles may be provided with an identification means for identifying the articles comprising different reagents (solid and/or liquid) from one another.

The identification means may, for example, comprise numbers, letters, symbols or colors in a coded combination, barcodes, chemical structures marked or printed punched card formats, ultraviolet-readable devices or any other readable device such as magnetic strips. The identification means may be provided by radiolabelling or the Irori labeling technology or by any convenient labeling technology known to the skilled person.

The articles may also include protective bands, or coverings. Since the article comprises polycrystalline diamond, the article may scratch and abrade surfaces of reactions vessels, which may damage the vessel and introduce contaminates from the reaction vessel into the reaction mixture. To mitigate this problem, a protective covering may be provided over parts of the article having surfaces and edges that may come in contact with the reaction vessel. In addition to preventing the article from scratching glassware, or other equipment in which the article may be used, the protective covering may also serve as an identification means. The covering should be applied so that it doesn't materially interfere with the reagent delivery and other functions of the article. The covering may be, for example, formed as a band around the edge of an article in the form of a tablet or coin, or formed as covers over the ends of a bar-cylinder. The covering should be essentially of a material that is inert in its intended environment and softer than the materials (usually glass) of the reactor in which it is to be used. Examples of suitable materials include, but are not limited to, polymeric materials, such as Teflon™, polypropylene, and corrosion resistant metals, such as noble metals (gold), certain stainless steels, and the like. An exemplary article 11 with a protective covering 13, and exposed surface 15 is shown in FIG. 1

Preparation of the Empty Articles

In an embodiment the articles are first prepared in an empty form (i.e. without a chemical reagent).

In an aspect of the invention, the polycrystalline diamond materials are sintered to form an article that is porous. The articles are porous in the sense that they are able to retain liquids in any form (organic, inorganic, hydrophilic, hydrophobic, viscous, non-viscous etc.). Since the articles are polycrystalline diamond, there is no substantial interaction between the sintered polycrystalline article and the retained liquid. In addition, the porosity is such that upon placement of the article in a selected fluid the retained liquid is able to be released from the article into the fluid, either quickly in a near instantaneous fashion, or continuously over a longer period of time. The article can also be designed such that rate of release of the retained liquid can also be set at a specific rate. A selected fluid may be a gas, a liquid, or a supercritical fluid.

Contemplated are articles having pores in the nanopore range (less than 2 nm) the micropore range (between about 2 nm and about 50 nm) and larger into the micron range. The pore size can be chosen depending on the liquid reagent desired to be retained, the desired absorption time of said reagent, and the desired amount which is to be retained in the reagent delivering article. Pore size of the polycrystalline diamond article has influence on absorption rate of the liquid reagent to be retained and vapor pressure of the article retaining a liquid reagent. Thus, a low pore size provides for lower vapor pressure and, conversely, a high pore size provides for a higher vapor pressure. Varying the pore size due to the vapor pressure is thus important when working with volatile hazardous substances, for example bromine or $CS_2$, for health reasons, when working with malodorous substances for well being and for increased retaining qualities. Likewise, a high pore size provides for a higher absorption rate and, conversely, a low pore size provides for a lower absorption rate. Ideally high absorption rates may be advantageous for speeding up the loading time for the loaded reagent delivering articles, but the absorption time may be compromised in order to avoid vaporization from the article when working with hazardous volatiles and/or malodorous substances and for increased keeping qualities. However, it should be noted that the pore size also has an impact on the release time for a particular reagent in a particular reaction medium. Therefore, the selection of a suitable pore size for a particular reagent delivering article is often a compromise between considerations to loading time, vaporization and release time.

The term "void volume" in the context of the polycrystalline article means that in terms of volume it may be seen as having an interstitial volume/available volume, which is defined as essentially all of the volume within the article that would be accessible to a fluid entering the article, i.e. the volume surrounded by the pore surfaces which does not contain the diamond material forming the article. The terms "interstitial volume", "available volume" and the "void volume" may be used interchangeably.

The polycrystalline diamond articles may comprise suitable void volumes as high as possible relative to the total volume of the article. For example, at least 20% (V/V), at least 30% (V/V), at least 40% (V/V), particularly at least 50% (V/V), at least 60% (V/V), and even at least 70% (V/V), most at least 80% (V/V) and in a particular embodiment at least 85% (V/V) depending on the intended application. In certain application, even a small amount, of a few percent, will be adequate.

The polycrystalline diamond article may be chosen so that the reagent delivering article contains a void volume corresponding to a desired predetermined amount of a liquid reagent to be retained therein.

The size of the article may vary depending on the intended application of said article, i.e. the larger the desired amount of reagent, the larger the article. Choosing the size of the article corresponding to the desired amount of liquid reagent to be retained therein is within the skill of the art. Thus the polycrystalline article is provided taking due consideration to void volume, pore size, intended loading and reagent etc.

After fabrication of the polycrystalline article, the surface properties of the diamond can be altered to provide activity to the surface.

Polycrystalline Diamond Articles with Reactive or Catalytic Properties

An embodiment is a polycrystalline diamond article with an active surface (i.e. on having catalytic or other reactive properties). The diamond surfaces of the polycrystalline diamond article can be treated to remove any reactivity, or to introduce a selected reactivity by attaching a reactive site or moiety to the surface. Methods for attaching reactive sites to diamond surfaces are known. Examples of such process are disclosed in U.S. patent application Ser. No. 10/322,863, filed 18 Dec. 2002, for Xu, et al., Publication No. 20040118762, titled "Packing Materials For Liquid Chromatography Using Chemically Modified Diamond Powders," which is hereby incorporated by reference.

The chemical moiety or reactive site bound to a diamond surface may for example serve as a carrier for a particular reaction taking place on the particular moiety, where a product may be released after one of more synthesis steps, or the reactive site may function as a catalyst or a scavenger.

Bound to the surface may be any suitable moiety that can be attached to the diamond surfaces. These include, but are not limited to catalysts, such as metals, metal ions, metal complexes and the like. In addition, the attached moiety may include functional groups that act as reagents, catalysts or scavengers. In Table I are shown examples of suitable functional groups that function as scavenger.

TABLE I

| | Functional Group | Examples of metals removed |
|---|---|---|
| | thiourea | Pd, Pt, Ru, Rh, Au, Ag, Cu, Hg, Pb, Cd, Ni, Co, Fe, V, Zn |
| | iminodiacetate | Cu, Al, Ga, In, V, Pb, Ni, Zn Cd, Be, Mn, Sr, Ba, Co, Fe |
| | aminomethyl-phosphoric acid | Fe, Cu, Ni, Al, Co, V |
| | benzylamine | Rh, Pd, Cu, Co, Ni |
| | imidazole | Rh, Co, Pd, Ni |
| | amine | Pd in basic media and with phosphines, Co, Ni, Rh |
| | thiol | Pd in acidic media and with phosphines, Co, Fe, Ni, Rh |
| | Imidazolylpropyl-amino | Pd, Ru, Os, Co, Ni, V, Rh, Cu, Fe, Sn |

TABLE I-continued

| Functional Group | | Examples of metals removed |
|---|---|---|
| (structure with SH on phenyl ring, NH linker) | mercaptophenyl-amino | Pd, Pt, Rh, Ni, Ru, Cu, Sn, Ag, Au, Cd, Hg, Pb |
| (structure with NH-CH2CH2-NH2) | aminoethylamino | Pd, Rh, V, Cu, Fe |
| (structure with propyl-NH2) | aminopropyl | Pd, Ru, Rh, Cu, Fe, Co, Ni |
| (structure with propyl-SH) | mercaptopropyl | Pd, Rh, Cu, Ru, Pt, Pb, Ag, Hg |
| (structure with propyl-NH-C(=S)-NH-Me) | methylthiourea | Pd, Rh, Cu, Ru, Pb, Fe, Co |
| (structure with propyl-NH-CH2CH2-NH-CH2CH2-NH2) | triamine | Pd, Rh, Co, Cu, Fe, Ru, Cd, Au, V, Zn, Pt |

Loading of Empty Articles

Before use in chemical reactions the prepared empty articles of polycrystalline diamond must be loaded with at least one reagent to be delivered. For example, the reagent delivering article may be loaded with liquid reagent by bringing the empty articles in contact with the liquid reagent.

If the reagent is liquid at ambient temperature it can be loaded by soaking the reagent delivering article in the liquid reagent, loading the liquid reagent manually or automatically using a pipette or by any other means suitable for supplying a liquid to a solid article. The liquid may also be supplied to the article under pressure either to reduce the absorption time or if the liquid is very viscous and is not readily absorbed in the article.

If the reagent is solid at ambient temperature the reagent may be dissolved in a suitable solvent and the resulting solution can be loaded into the article as above. It may be advantageous to remove the solvent by evaporation after the loading.

Alternatively, if the reagent is solid at ambient temperature it may be melted and loaded into the articles as above. After the loading the articles may be cooled to ambient temperature where the reagent will solidify inside the articles. Usually the solidified reagent will dissolve in the reaction medium at a satisfactory rate from the loaded articles. This method may be applied for reagents having a sufficient stability at the melting temperature and requires further that the polycrystalline diamond be stable at said melting temperature, which usually is not a problem.

If the reagent is a gas at ambient temperature the reagent may be liquefied at low temperature and loaded at low temperature. After loading it may be necessary to store the loaded articles at low temperature in order to avoid unsatisfactory high evaporation of the loaded reagent.

Even though most reagents are easily loaded into the reagent delivering articles a few reagents may resist loading by capillary force alone. If such difficulties are encountered the reagents may be loaded by application of higher pressure to the container in where the loading takes place, or by using a different reagent delivering article with different a pore size.

For a given size and composition of a particular article, a particular amount of reagent is loaded in the article with high reproducibility. Thus if several articles are loaded with the same reagent all the loaded articles will contain approximately the same amount of the liquid reagent. It has been estimated that the variance in content of loaded reagent from one loaded reagent delivering article to another loaded reagent delivering article in a series of loading the same reagent delivering articles with same reagent usually is less than 5%.

Reagents to be included in the empty articles include organic reagents, inorganic reagents and metalorganic compounds. The reagents may be neutral compounds or salts.

The reagent delivering article may even be loaded with more than one reagent(s) (e.g., by loading a mixture of the reagents into the articles). Alternatively, a liquid reagent may be loaded in a porous article containing functionalized groups bound to the surface. In this way the article may e.g. provide more than one reagent to a reaction, may provide one or more reagents and functionalized groups or may provide one or more reagents as well as a catalyst.

As the organic reagent can be used liquid organic substances or solid organic substances dissolved in a suitable solvent, it will be within the skills of the average practitioner to select a suitable solvent for a particular reagent. As examples of suitable solvents can be mentioned water, ethanol, dimethylformamide, ethanol, tetrahydrofuran etc.

Examples of organic liquid substances include both aliphatic and aromatic substances and include but are not limited to substituted aromatic rings such as m-nitrotoluene, m-bromoaniline, m-fluorophenol, 3,4-dichlorobenzylchloride, o-iodoanisole, phenylisocyanate; aromatic hetero rings such as pyridines, e.g. m-bromopyridine; aliphatic non-cyclic compounds such as hexamethylphosphoroustriamide (HMPA), diethylazodicarboxylate (DEAD), butanic acid, diiodomethane, iodomethane and aliphatic cyclic compounds such as 15-crown-5.

Examples of organic solids include but are not limited to benzotriazol-1-yl-oxytripyrrolidinophosphonium hexafluorophosphate (PyBOP), copper (II) pivaloate, BiPh3 and PhSeSePh.

The inorganic liquid can be used liquid inorganic substances or solid inorganic substances dissolved in a solvent. Examples of inorganic liquids include, but are not limited to, $H_2O_2$ as a stable aqueous solution, $Br_2$, $CS_2$ and polymeric siloxanes such as polymeric dimethoxysiloxane.

Examples of inorganic solids that may be dissolved in a solvent e.g. water before loading include but are not limited to $K_2Cr_2O_7$, $B_{10}H_{14}$, $CuSO_4.5H_2O$, $HgCl_2$, $ZnCl_2$, $Li-ClO_4$, $Cs_2CO_3$, $CeCl_3.7H_2O$, $SnCl_2.2H_2O$, $NH_4^+PF_6^-$, $K_2CO_3$, $Cu(NO_3)_2.3H_2O$, $KCN$, $FeCl_3$, $S_8$, $BiCl_3$ and $NH_4$, $^+SO_3NH_2^-$.

The selection of solvent to be used for loading a solid reagent as a solution depends on the particular reagent. Thus the solvent should be selected under due consideration of the solubility of the reagent in the solvent. It is within the skills of the average practitioner to select a suitable solvent for a particular reagent and an intended reaction. If desired, different solvents for a particular reagent may be evaluated using simple comparable tests.

Usually the solvent is evaporated after loading a solution of a reagent into a reagent delivering article. It may, in particular circumstances, be possible to load a reagent delivering article with a solution of a reagent, followed by evaporation of the solvent and an additional loading with the same or a different liquid reagent. The evaporation of solvent and reloading may even be performed repeatedly.

Having the liquid reagent retained in the article provides for several advantages in respect of handling and manual distribution of chemicals. Articles retaining reagents evade handling large flasks containing liquid reagents and the concomitant exposure to in particular hazardous chemicals providing for a safer working environment for those working in the chemical industry.

In an embodiment the liquid reagent is loaded immediately before use of the article. Thus, for example a sufficient number of articles for a days work may be loaded in the morning and used same day. There may even exist situations where a more frequent loading is desired. This embodiment may be advantageous when the reagent in question is unstable or when the use thereof is infrequent.

Alternatively a larger portion of reagent delivering articles may be loaded periodically (e.g. weekly, monthly or less frequently) depending of the keeping properties of the liquid reagent in question. For certain combinations of reagent delivering article and reagent the loaded articles may be stored for several months or even years without any significant loss of reactivity. This embodiment is advantageous when the reagent in question is frequently used and shows a satisfactory stability.

As mentioned above, loading the article with reagent can be accomplished both manually and automatically. When the reagent delivering articles are loaded automatically, human contact with hazardous substances to be used when working in the laboratory, particularly when working with organic synthesis, is substantially minimized or avoided completely.

Automatic loading furthermore provides for a commercial production of both standard and custom-made articles that are ready for use in the chemical industry and/or research laboratories.

In another embodiment the article is coated with a coating substance in order to further seal said article against environmental exposure in case the article is loaded with a volatile or labile liquid reagent and/or to protect the environment (e.g. laboratory workers) from fumes descending from the article. This is particularly useful if said article is loaded with very volatile substances that are hazardous to the environment and which are not retained sufficiently by choosing low pore sizes of the polycrystalline diamond.

Coating the article may further protect the loaded reagent against deterioration due to exposure to ambient air, and will further reduce exposure of the staff handling the articles to the reagent.

The coating substance may include any suitable substance that does not react with the reagent retained in the article, and does not react or interfere with the reaction taking place in the solution. To allow release of the retained reagent, the coating may also need to be soluble in order to dissolve when the article is placed into the solution.

Coating substances for the inventive article can be any suitable conventional coating substance known in the art. The skilled person is capable of selecting suitable coating substances with due considerations to the reagent in the reagent delivering article and the intended reaction.

Filled Articles

For reagents that can survive the conditions for forming a sintered diamond article, it is contemplated that filled articles be fabricated by incorporating the reagent into the diamond material before sintering. This embodiment may be used if it is desired to include a solid active compound into the reagent delivering article, for example a metal (e.g., cobalt, nickel, iron, etc.) or a catalyst. In addition, it is contemplated that polycrystalline diamonds be bound by other means other than by sintering. For example, polycrystalline diamonds can be bound together by a suitable polymer. This can be accomplished by suitable mixing, and tabletting or compression processes.

Optionally reactive solids or solid active substances can be added before compression into the article. Further, a liquid reagent may be added to the mixture, so that as the articles are formed, they are preloaded with the liquid reagent.

Another suitable method for forming polymer bound polycrystalline articles is disclosed in U.S. Provisional Patent Application No. 61/052,185, filed 10 May 2008, and titled "Synthesis of Porous Diamond Particles", which is hereby incorporated by reference.

It may even be possible to reuse reagent delivering articles. After a first use the reagent delivering article may be purified from remnants of the first reaction medium (e.g. by washing one or more times or by burning out the organic content). After the purification the reagent delivering articles may be reloaded and used for delivering reagent to a new chemical reaction.

The porous diamond article can be combined with a magnetic stir bar to help dissolve a reagent it contains.

The porosity of the diamond may be increased by treatment with radiation, such as alpha particles.

What is claimed is:

1. A reagent delivering article, comprising:
   porous sintered polycrystalline diamond including pores formed therein;

a chemically active agent loaded in the pores of the porous sintered polycrystalline diamond;
a removable coating substance coating the porous sintered polycrystalline diamond such that the chemically active agent therein is substantially sealed from an environment;
a protecting covering over only a portion of the reagent delivering article to protect surfaces from being damaged by the reagent delivering article, the protecting covering including at least one of polytetrafluoroethylene, polypropylene, or a noble metal; and
wherein the delivering article is capable of retaining the chemically active agent and releasing the chemically active agent in a fluid.

2. The article of claim 1, wherein the fluid is a liquid, or a gas, or a supercritical fluid.

3. The article of claim 1, wherein the porous sintered polycrystalline diamond has a surface with reactive sites.

4. The article of claim 3, wherein the reactive sites are catalytically active.

5. The article of claim 3, wherein the reactive sites are metal sequestration sites.

6. The article of claim 1, wherein the chemical reagent is retained in the form of a liquid.

7. The article of claim 1, wherein the chemical reagent is retained in the form of a solid.

8. The article of claim 1, wherein the chemically active agent is retained as active sites on a surface of the porous sintered polycrystalline diamond.

9. The article of claim 1, further comprising active sites on surfaces of the porous sintered polycrystalline diamond.

10. A method for introducing reagent to a reaction medium comprising introducing into the reagent into the reagent delivering article of claim 1.

11. The method of claim 10, wherein the porous sintered polycrystalline diamond includes reactive sites including one or more of catalysts, sequestration agents, pharmaceutically active agents, or reagents.

12. A reagent delivering article, comprising:
porous sintered polycrystalline diamond;
a coating over the porous sintered polycrystalline diamond such that the porous sintered polycrystalline diamond is substantially sealed from an environment;
a protecting covering over only a portion of the reagent delivering article to protect surfaces from being damaged by the reagent delivering article, the protecting covering including at least one of polytetrafluoroethylene, polypropylene, or a noble metal; and
wherein surfaces of the sintered polycrystalline diamond have been treated to impart reactive sites to the surfaces; and
wherein the porous sintered polycrystalline diamond exhibits a pore size of less than about 2 nm.

13. The article of claim 12, wherein the reactive sites are one or more of chemically active agents, or reagents.

14. A method for manufacturing the reagent delivering article, the method comprising:
forming from polycrystalline diamond, the porous polycrystalline diamond of claim 1 that is capable of retaining the chemically active agent;
retaining the chemically active agent in the porous polycrystalline diamond.

15. The method of claim 14, wherein the forming comprises forming the porous polycrystalline diamond by sintering.

16. The method of claim 15, wherein the retaining comprises applying active sites on surfaces of the porous polycrystalline diamond.

17. The method claim 14, wherein the porous polycrystalline diamond is capable is retaining a liquid and retaining comprises loading the liquid in the porous polycrystalline diamond.

18. The method as in claim 14, wherein the forming comprises compressing a mixture of the polycrystalline diamond and a polymer.

19. The method as in claim 18, wherein the retaining comprises including the reagent in the mixture.

* * * * *